United States Patent
Wang et al.

(10) Patent No.: US 7,163,522 B1
(45) Date of Patent: *Jan. 16, 2007

(54) BLOCK COPOLYMER ELASTOMER CATHETER BALLOONS

(75) Inventors: Lixiao Wang, Maple Grove, MN (US); Jianhua Chen, Plymouth, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 539 days.

This patent is subject to a terminal disclaimer.

(21) Appl. No.: 09/712,042

(22) Filed: Nov. 14, 2000

Related U.S. Application Data

(60) Continuation of application No. 09/320,792, filed on May 27, 1999, now Pat. No. 6,146,356, which is a division of application No. 08/811,761, filed on Mar. 6, 1997, now Pat. No. 6,171,278, which is a continuation-in-part of application No. 08/805,899, filed on Feb. 25, 1997, now Pat. No. 5,830,182, which is a continuation of application No. 08/671,861, filed on Jun. 28, 1996, now abandoned, which is a continuation of application No. 08/397,837, filed on Mar. 2, 1995, now Pat. No. 5,556,383, which is a continuation-in-part of application No. 08/204,554, filed on Mar. 2, 1994, now abandoned.

(51) Int. Cl.
*A61M 29/02* (2006.01)
*A61M 29/00* (2006.01)

(52) U.S. Cl. .................. 604/96.01; 604/524; 606/192; 428/35.7

(58) Field of Classification Search ............. 604/96.01, 604/104; 606/192–194; 428/35.7; 525/458
See application file for complete search history.

(56) References Cited

U.S. PATENT DOCUMENTS

| 4,154,244 A | 5/1979 | Becker et al. .......... 128/349 B |
| 4,254,774 A | 3/1981 | Boretos | |

(Continued)

FOREIGN PATENT DOCUMENTS

EP    0 485 903    5/1982

(Continued)

OTHER PUBLICATIONS

"Thermoplastic Elastomer," Kagaku Kogyo Nipposha, published Feb. 15, 1992, pp. 23-39 and 225-229 with partial translation.

(Continued)

*Primary Examiner*—Nicholas D. Lucchesi
*Assistant Examiner*—Melissa A. McCorkle
(74) *Attorney, Agent, or Firm*—Vidas, Arrett&SteinkrausPA

(57) ABSTRACT

Balloons for medical devices, particularly balloon agioplasty catheters, which have hybrid compliance curves in which growth rate slows at higher pressures are made from block copolymer thermoplastic elastomers.

27 Claims, 3 Drawing Sheets

U.S. PATENT DOCUMENTS

| | | | |
|---|---|---|---|
| 4,331,786 A | | 5/1982 | Foy et al. |
| 4,332,920 A | | 6/1982 | Foy et al. |
| 4,385,635 A | | 5/1983 | Ruiz |
| 4,413,989 A | | 11/1983 | Schjeldahl et al. ............ 604/96 |
| 4,490,421 A | * | 12/1984 | Levy ........................... 604/96 |
| 4,563,181 A | | 1/1986 | Wijaymachna |
| 4,675,361 A | | 6/1987 | Ward, Jr. ..................... 525/92 |
| 4,786,556 A | | 11/1988 | Hu et al. ..................... 428/412 |
| RE32,983 E | * | 7/1989 | Levy ........................... 604/96 |
| 4,886,506 A | | 12/1989 | Lovgren et al. |
| 4,898,591 A | | 2/1990 | Jang et al. |
| 4,906,244 A | * | 3/1990 | Pinchuk et al. ............. 606/194 |
| 4,917,667 A | | 4/1990 | Jackson |
| 4,938,676 A | * | 7/1990 | Jackowski et al. .......... 425/140 |
| 4,950,239 A | | 8/1990 | Gahara et al. ............... 604/96 |
| 4,950,257 A | | 8/1990 | Hibbs et al. |
| 4,952,357 A | | 8/1990 | Euteneuer .................... 264/129 |
| RE33,561 E | * | 3/1991 | Levy ........................... 604/96 |
| 5,108,415 A | | 4/1992 | Pinchuk et al. |
| 5,156,612 A | | 10/1992 | Pinchuk et al. |
| 5,195,969 A | | 3/1993 | Wang et al. |
| 5,236,659 A | | 8/1993 | Pinchuck et al. |
| 5,250,069 A | | 10/1993 | Nobuyoshi et al. |
| 5,254,090 A | * | 10/1993 | Lombardi et al. ....... 604/96.01 |
| 5,254,091 A | | 10/1993 | Aliahmad et al. |
| 5,270,086 A | * | 12/1993 | Hamlin ....................... 428/35.2 |
| 5,281,677 A | * | 1/1994 | Onwunaka et al. ......... 525/458 |
| 5,290,306 A | | 3/1994 | Trotta et al. |
| 5,295,978 A | | 3/1994 | Fan et al. .................... 604/265 |
| 5,300,048 A | | 4/1994 | Drewes, Jr. et al. ........ 604/280 |
| 5,304,134 A | | 4/1994 | Kraus et al. .................. 604/96 |
| 5,304,340 A | | 4/1994 | Downey |
| 5,316,016 A | | 5/1994 | Adams et al. |
| 5,328,468 A | * | 7/1994 | Kaneko et al. ............... 604/96 |
| 5,334,146 A | | 8/1994 | Ozasa |
| 5,335,675 A | | 8/1994 | Wheeler et al. ............ 128/842 |
| 5,342,386 A | | 8/1994 | Trotta |
| 5,344,400 A | * | 9/1994 | Kaneko et al. ............... 604/96 |
| 5,348,538 A | | 9/1994 | Wang et al. ................... 604/96 |
| 5,397,306 A | | 3/1995 | Nobuyoshi et al. .......... 604/96 |
| 5,403,340 A | | 4/1995 | Wang et al. |
| 5,411,477 A | | 5/1995 | Saab |
| 5,458,935 A | * | 10/1995 | Alzner ....................... 428/35.7 |
| 5,478,320 A | | 12/1995 | Trotta |
| 5,500,180 A | | 3/1996 | Anderson et al. ........... 264/532 |
| 5,500,181 A | | 3/1996 | Wang et al. |
| 5,512,051 A | | 4/1996 | Wang et al. |
| 5,545,133 A | * | 8/1996 | Burns et al. .................. 604/96 |
| 5,554,120 A | * | 9/1996 | Chen et al. ............... 604/96.01 |
| 5,556,383 A | | 9/1996 | Wang et al. |
| 5,565,523 A | | 10/1996 | Chen et al. ................... 525/176 |
| 5,769,817 A | * | 6/1998 | Burgmeier ................... 604/96 |
| 5,807,520 A | | 9/1998 | Wang |
| 5,830,182 A | * | 11/1998 | Wang et al. ............. 604/96.01 |
| 5,879,369 A | * | 3/1999 | Ishida ......................... 604/96 |
| 5,921,957 A | * | 7/1999 | Killion et al. ................ 604/96 |
| 5,951,941 A | | 9/1999 | Wang et al. |
| 6,086,556 A | * | 7/2000 | Hamilton et al. ........ 604/96.01 |
| 6,146,356 A | * | 11/2000 | Wang et al. ............. 604/96.01 |
| 6,171,278 B1 | * | 1/2001 | Wang et al. ................ 604/104 |
| 6,210,364 B1 | | 4/2001 | Anderson et al. |
| 6,242,063 B1 | * | 6/2001 | Ferrera et al. ............. 428/35.2 |

FOREIGN PATENT DOCUMENTS

| | | |
|---|---|---|
| EP | 0 349 640 B1 | 2/1988 |
| EP | 0 318 919 | 6/1989 |
| EP | 381919 | 6/1989 |
| EP | 0 436 501 | 7/1991 |
| EP | 0 537 069 A1 | 10/1992 |
| EP | 0 513 459 A1 | 11/1992 |
| EP | 0 566 755 A1 | 10/1993 |
| EP | 592870 | 4/1994 |
| EP | 606165 | 7/1994 |
| FR | 2 651 681 | 3/1991 |
| JP | 3-176068 | 7/1991 |
| JP | 4-144572 | 5/1992 |
| WO | 84/01513 | 1/1984 |
| WO | W0 89/08473 | 9/1989 |
| WO | WO 92/08512 | 5/1992 |
| WO | WO 92/19440 | 11/1992 |
| WO | WO 95/22367 | 8/1995 |
| WO | WO 96/04951 | 2/1996 |
| WO | WO 96/12516 | 5/1996 |

OTHER PUBLICATIONS

*Ullmann's Encyclopedia of Industrial Chemistry* (1995), vol. A26, Cpt 4, "Thermoplastic Elastomers," pp. 651-655.

Tecoflex® Medical Grade Aliphatic Thermoplastic Polyurethanes, date unknown.

Scimed Leap Trio PTCA Catheters, May 16, 1995.

Dow Processing Guide, Pellethane, date unknown.

Dupont product literature on HYTREL, date unknown.

Dow Chemical product literature on ISOPLAST. Dec. 17, 1991 and other dates unknown.

Tecothane® Medical Grade Aliphatic Thermoplastic Polyurethanes, date unknown.

Thermopolastic Elastomer data sheet, D.A.T.A. Business Publishing. p. 2-1709 1994.

Polyamide-Nylon data sheet, D.A.T.A. Business Publishing, p. 2-595 1994.

International Serach Report. International Application PCT/US 95/02717.

Polyether Block Amide data sheet, D.A.T.A. Business Publishing, p. 2-837 1994.

Tecoplast™ Engineering Polyurethane Resins May 1996.

U.S. Appl. No. 08/811,761, filed Mar. 6, 1997, Wang et al.

U.S. Appl. No. 08/805,899, filed Feb. 25, 1997, Wang et al.

U.S. Appl. No. 08/397,837, filed Mar. 2, 1995, Wang et al.

U.S. Appl. No. 09/320,792, filed May 27, 1999, Wang et al.

\* cited by examiner

BLOCK COPOLYMER ELASTOMER CATHETER BALLOONS

CROSS REFERENCE TO RELATED APPLICATIONS

This application is a continuation of application Ser. No. 09/320,792, filed May 27, 1999, now U.S. Pat. No. 6,146,356 issued on Nov. 14, 2000, which is a division of application Ser. No. 08/811,761, filed Mar. 6, 1997 now U.S. Pat. No. 6,171,278, incorporated herein by reference; which is a continuation-in-part of application Ser. No. 08/805,899, filed Feb. 25, 1997, now U.S. Pat. No. 5,830,182; which is a continuation of application Ser. No. 08/671,861, filed Jun. 28, 1996, now abandoned; which is a continuation of application Ser. No. 08/397,837 filed Mar. 2, 1995, now U.S. Pat. No. 5,556,383; which is a continuation-in-part of application Ser. No. 08/204,554, filed Mar. 2, 1994, now abandoned. All of the above cited applications are herein incorporated by reference in their entirety.

BACKGROUND OF THE INVENTION

Balloons mounted on the distal ends of catheters are widely used in medical treatment. The balloon may be used widen a vessel into which the catheter is inserted or to force open a blocked vessel. The requirements for strength and size of the balloons vary widely depending on the balloon's intended use and the vessel size into which the catheter is inserted. Perhaps the most demanding applications for such balloons are in balloon angioplasty in which catheters are inserted for long distances into extremely small vessels and used to open stenoses of blood vessels by balloon inflation. These applications require extremely thin walled high strength relatively inelastic balloons of predictable inflation properties. Thin walls are necessary because the balloon's wall and waist thicknesses limit the minimum diameter of the distal end of the catheter and therefore determine the limits on vessel size treatable by the method and the ease of passage of the catheter through the vascular system. High strength is necessary because the balloon is used to push open a stenosis and so the thin wall must not burst under the high internal pressures necessary to accomplish this task. The balloon must have some elasticity so that the inflated diameter can be controlled, so as to allow the surgeon to vary the balloon's diameter as required to treat individual lesions, but that elasticity must be relatively low so that the diameter is easily controllable. Small variations in pressure must not cause wide variation in diameter.

While angioplasty balloons are considered inelastic relative to balloons used in most other applications, there is in the art a general classification of such balloons based on their expandability or "compliance" relative to each other. As used herein, "non-compliant" balloons are the least elastic, increasing in diameter about 2–7%, typically about 5%, as the balloon is pressurized from a inflation pressure of about 6 atm to a pressure of about 12 atm, that is, they have a "distension" over that pressure range of about 5%. "Semi-compliant" balloons have somewhat greater distensions, generally 7–16% and typically 10–12% over the same pressurization range. "Compliant" balloons are still more distensible, having distensions generally in the range of 16–40% and typically about 21% over the same pressure range. Maximum distensions, i.e. distension from nominal diameter to burst, of various balloon materials may be significantly higher than the distension percentages discussed above because wall strengths, and thus burst pressures, vary widely between balloon materials. The 6–12 atm inflation range is used in the present application to allow direct comparison of the compliance attributes of various balloons.

The strength of the polymer materials used in the balloons varies widely. The strongest balloons are also the most inelastic, being made of highly orientable polymers such as polypropylene, polyethylene terephthalate or other phthalate polyesters or copolyesters, and nylons. Tensile wall strengths are commonly 20,000–50,000 psi. Commercial angioplasty balloons made of such materials with nominal diameters in the range of 1.5–4.5 mm have distensions in the non-compliant to semi-compliant range and can often be rated to pressures of 16 atm or higher without risk of bursting (actual burst pressures may exceed 20 atm). Generally, however, as compliance increases the wall strength decreases. Other semi-compliant and compliant balloons are made of less highly orientable polymers such as ethylene-vinyl acetate, polyvinyl chloride, olefin copolymers and ionomer resins. The wall strengths of balloons made from these less orientable materials are still lower than those made from the highly orientable polymers, commonly in the range of 6,000–15,000 psi, resulting in lower rated maximum inflation pressures of 9–10 atm.

The particular distension and maximum pressure attributes of a balloon are also influenced both by polymer type and by the conditions under which the balloon is blown. Angioplasty balloons are conventionally made by blowing a tube of polymer material at a temperature above its glass transition temperature. For any given balloon material, there will be a range of distensions achievable depending on the conditions chosen for the blowing of the balloon.

In U.S. Pat. No. 4,906,244 to Pinchuck there are described balloons of nylon (i.e. aliphatic polyamide) materials, such as nylon 12, nylon 11, nylon 9, nylon 6/9 and nylon 6/6. Like all other polymer materials the distensions of these balloons can be determined, within a range, by controlling blowing conditions such as initial dimensions of tubing, prestretching, hoop ratio and heat set conditions. The data in the reference show that compliance characteristics can be obtained ranging from non-compliant to semi-compliant characteristics and that wall strengths of greater than 15,000 can be obtained. The reference suggests that higher compliances can be achieved with nylon materials but there is no indication of what other nylons or other balloons forming conditions could be employed to do so.

It has also been suggested to prepare balloons of thermoplastic elastomers in U.S. Pat. No. 4,254,774 to Boretos, and polyamide elastomers have been mentioned among a number of possible balloon materials suggested in U.S. Pat. No. 5,250,069 to Nobuyoshi, et al, but there are many of such thermoplastic elastomer polymers and before the invention hereof it has been expected that performance of balloons made from these materials would not be generally any better than high to intermediate compliance made from conventional thermoplastic polymers such as polyethylene ionomer, polyvinyl chloride, polyethylene or ethylene-vinyl acetate.

In U.S. Pat. No. 5,290,306 polyester ethers and polyether-esteramide polymers of Shore D hardness less than 55 have been proposed for use as a sleeve or co-extruded outer layer to a balloon of a biaxially oriented nylon or polyethylene terephthalate (PET) material, so as to provide the balloon with improved softness and pin-hole and abrasion resistance.

Polyurethane block copolymers having flexural modulus of about 190,000 and an ultimate elongation of 250% are disclosed as balloon materials in EP 0592885 and mention is made of also using polyester block copolymers or polyamide block copolymers but no suggestion is made that such alternative copolymers could be usefully employed if their flexural modulus was substantially lower or their ultimate elongation was substantially higher than the disclosed polyurethane block copolymers.

SUMMARY OF THE INVENTION

New balloon materials, which possess a unique combination of physical properties including non-compliant, semi-compliant and compliant distension attributes, good flexibility and high tensile strength, are made from particular block copolymer thermoplastic elastomers. Preferred such block copolymer elastomers are characterized as follows:

the block copolymer is made up of hard segments of a polyester or polyamide and soft segments of polyether;

the polyester hard segments are polyesters of an aromatic dicarboxylic acid and a $C_2$–$C_4$ diol, the polyamide hard segments are polyamides of $C_6$ or higher, preferably $C_{10}$–$C_{12}$, carboxylic acids and $C_6$ or higher, preferably $C_{10}$–$C_{12}$, organic diamines or of $C_6$ or higher, preferably $C_{10}$–$C_{12}$, aliphatic ω-amino-α-acids, and the polyether soft segments are polyethers of $C_2$–$C_{10}$, preferably $C_4$–$C_6$ diols;

the block copolymer has a low flexural modulus, namely less than 150,000 psi, preferably less than 120,000 psi;

the block copolymer has a hardness, Shore D scale, of greater than 60; and the percentage by weight of the block polymer attributable to the hard segments is between about 50% and about 95%.

From such polymers, balloons having compliant to semi-compliant expansion profiles can be prepared with wall strengths greater than 150,000 psi, frequently greater than 20,000 psi. The high strength of the balloons produced from the polymers allows for construction of low profile catheters and the low flexural modulus contributes to a softer feel found with the balloons of the invention, compared to those made of other high strength polymer materials. Low profile catheters made with the inventive balloons have very good initial crossing, good trackability and good recrossing after first inflation.

A further embodiment of this invention includes balloons made from block copolymers which display a compliance curve, with two generally linear segments, the higher pressure segment of which provides a substantially reduced growth rate with increasing pressure than the lower pressure segment.

A still further embodiment of this invention includes balloons made from various melt blend products of flexible block copolymers and relatively rigid engineering polymers which are structurally similar to a block of the flexible block copolymer. Such blends provide a mechanism for modifying the range of available compliance and strength properties of medical device balloons.

DETAILED DESCRIPTION OF THE INVENTION

Figure 1:
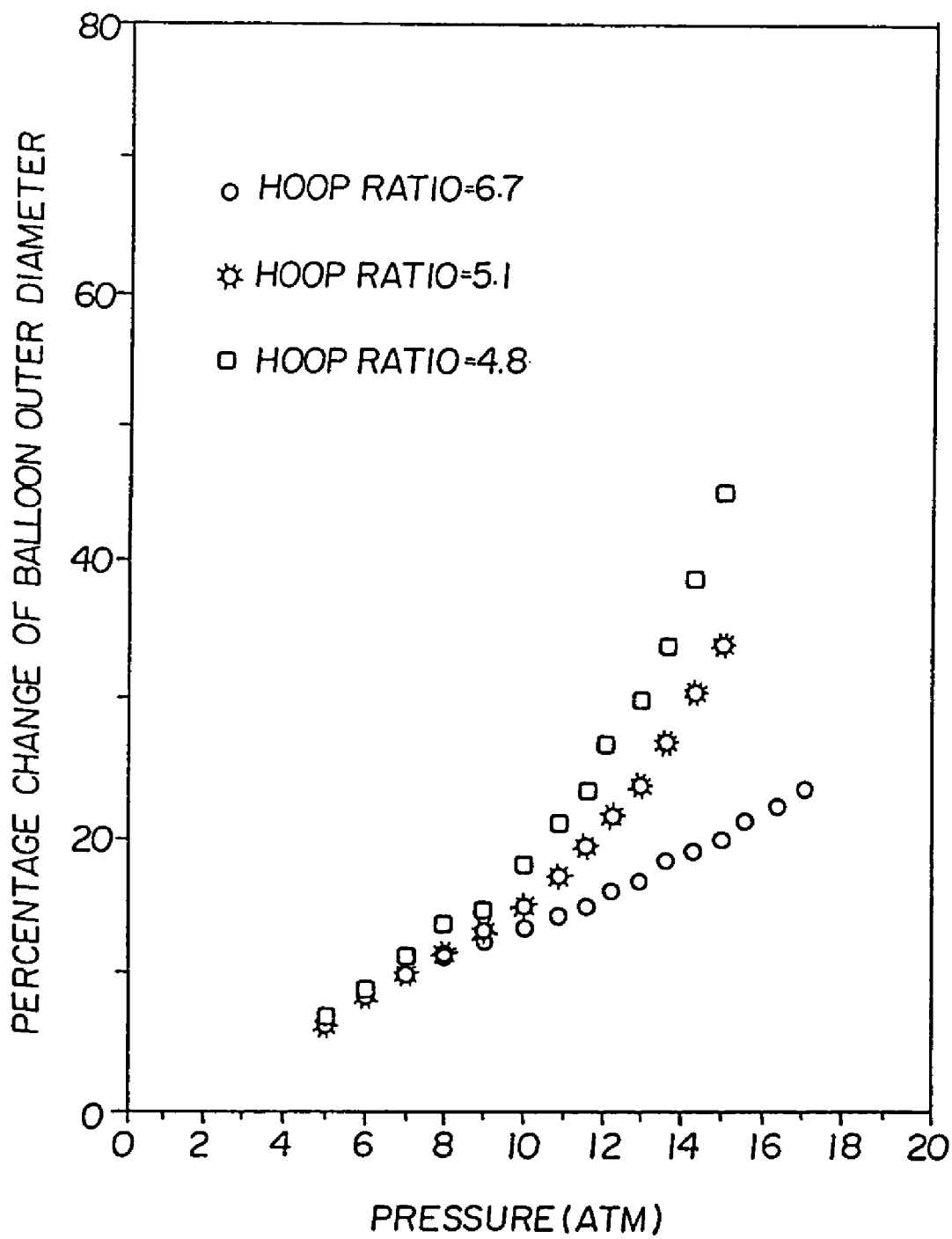
FIG. 1 is a graph of the distension from nominal diameter to burst of several balloons of the invention prepared from a polyamide/polyether polyester block copolymer using different hoop ratios to form the balloon.

It should be noted here that, with respect to the block copolymers described herein, the individual polymeric segments which make up the block copolymers are typically of insufficient size to constitute suitable thermoformable materials and in that sense the segments may be considered oligomers. Thus, the block copolymers are very different, non-equivalent, materials from the commercial thermoformable polymers of same structural types as the individual blocks which make up the block copolymers.

The preferred balloons of the invention are made of polyamide/polyether block copolymers. The polyamide/polyether block copolymers are commonly identified by the acronym PEBA (polyether-block-amide). The polyamide and polyether segments of these block copolymers may be linked through amide linkages, however, most preferred are ester linked segmented polymers, i.e. polyamide-polyether-polyesters. Such polyamide/polyether/polyester block copolymers are made by a molten state polycondensation reaction of a dicarboxylic polyamide and a polyether diol. The result is a short chain polyester made up of blocks of polyamide and polyether. The polyamide and polyether blocks are not miscible. Thus the materials are characterized by a two phase structure: one is a thermoplastic region that is primarily polyamide and the other is elastomer region that is rich in polyether. The polyamide segments are semicrystalline at room temperature. The generalized chemical formula for these polyester polymers may be represented by the following formula:

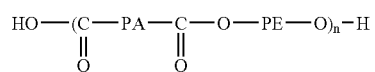

in which PA is a polyamide segment, PE is a polyether segment and the repeating number n is between 5 and 10.

The polyamide segments are suitably aliphatic polyamides, such as polyamides 12, 11, 9, 6, 6/12, 6/11, 6/9, or 6/6. Most preferably they are polyamide 12 segments. The polyamide segments may also be based on aromatic polyamides but in such case significantly lower compliance characteristics are to be expected. The polyamide segments are relatively low molecular weight, generally within the range of 500–8,000, more preferably 2,000–6,000, most preferably about 3,000–5,000.

The polyether segments are aliphatic polyethers having at least 2 and no more than 10 linear saturated aliphatic carbon atoms between ether linkages. More preferably the ether segments have 4–6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1000.

The weight ratio of polyamide to polyether in the polyamide/polyether polyesters used in the invention desirably should be in the range of 50/50 to 95/5, preferably between 60/30 and 92/08, more preferably, between 70/30 and 90/10.

Polyamide/polyether polyesters are sold commercially under the PEBAX trademark by Atochem North America, Inc., Philadelphia Pa. Examples of suitable commercially available polymers are the Pebax® 33 series polymers with hardness 60 and above, Shore D scale, especially Pebax® 7033 and 6333. These polymers are made up of polyamide 12 segments and poly(tetramethylene ether) segments in about 90/10 and about 80/20 weight ratios, respectively. The average molecular weight of the individual segments of polyamide 12 is in the range of about 3,000–5,000 grams/mole and of the poly(tetramethylene ether) segments are in the ranges of about 750–1,250 for the 6333 polymer and about 500–800 for the 7033 polymer. The inherent viscosities of these polymers are in the range of 1.33 to 1.50 dl/g.

Generally speaking, balloons of the Pebax® 7033 type polymer exhibit borderline non-compliant to semi-compliant behavior and balloons of Pebax® 6333 type polymer show semi-compliant to compliant distension behavior, depending on the balloon forming conditions.

While the Pebax®-type polyamide/polyether polyesters are most preferred, it is also possible to use other PEBA polymers with the physical properties specified herein and obtain similar compliance, strength and softness characteristics in the finished balloon.

As an alternative to polyamide elastomers, it is also possible to utilize polyester/polyether segmented block copolymers and obtain similar balloon properties. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol.

Suitable dicarboxylic acids used to prepare the polyester segments of the polyester-polyether block copolymers are ortho-, meta- or para- phthalic acid, napthalenedicarboxylic acid or meta-terphenyl-4,4'-dicarboxylic acids.

Preferred polyester/polyether block copolymers are poly(butylene terephthalate)-block-poly(tetramethylene oxide) polymers such as Arnitel EM 740, sold by DSM Engineering Plastics. Hytrel polymers, sold by DuPont which meet the physical and chemical specifications set out herein can also be used, but are less preferred.

It is believed important that the block copolymers have a hardness, Shore D scale, of at least 60 and a flexural modulus of no more than about 150,000, in order to obtain the desirable combination of strength, compliance and softness characteristics which distinguish the inventive balloons. Preferably the Shore D hardness is in the range of 65–75 and the flexural modulus is in the range of 50,000–120,000. The preferred polymers useful in the invention are also characterized by a high ultimate elongation of about 300% or higher and an ultimate tensile strength of at least 6,000 psi.

The ballooons of the invention are made using known techniques for forming catheter balloons. For coronary angioplasty catheter balloons (balloon diameters of about 1.5–4.0 mm), single wall thicknesses of less than 0.001 inches, preferably less than 0.0007 inches, are readily obtained. Wall strengths for such balloons are in excess of 15,000, typically at least 18,000 psi, and in most cases in the range of about 20,000 to 32,000 psi. For peripheral angioplasty, balloons of up to 10 mm diameter may be used and in such cases somewhat thicker walls may be employed. Even with a 10 mm balloon, wall thicknesses of about 0.0015 mm or less can be employed to provide balloons with burst pressures of at least 10 atm. Suitably the balloons are formed by expansion of tubing at a hoop ratio (mold diameter/tubing ID) of between 3 and 8, preferably between 4 and 7.

The following examples illustrate the preparation and unique properties of balloons of the invention.

EXAMPLES

Tubing Extrusion:

In these examples all tubing materials were made by extrusion. Polymer pellets were dried to less than 0.10 wt % moisture content before extrusion. Tubing was extruded at melt temperature range of 200° C. to 220° C. by hot feedthroat through seven extruder zones with controlled temperatures. The extrusion conditions were based upon manufacturer's recommended polymer processing conditions. After the polymer material extruded out of the die in tube form it passed through a small air gap and was cooled in a deionized water bath maintained at about 65° F. A puller was used to pull the tube through the water bath. After passing through the puller, the extruded tubing was cut into 8 inch sections or spooled. A variety of tubing sizes were made by this method.

Example 1

The product of this example is a 2.25 mm balloon made from Pebax® 7033. This polymer has a Shore D hardness of 69, a flexural modulus of 67,000, an ultimate tensile strength of 8,300 psi and an ultimate elongation of 400%. The tubing sections had an OD of 0.0270 inch and an ID of 0.0179 inch. In order to form a 2.25 mm balloon with a 20 mm body length, a mold having dimensions that allowed the tube to blow out to the appropriate body size and balloon waist inner diameters was used.

After the tubing section was securely inside the mold, the mold was placed in a holder. The tubing section extended out the top of the mold and was fed into a Touhy clamp through which nitrogen gas applied to the inner lumen of the tubing at 280 psi with tension applied to the tubing. The tubing section at the bottom of the mold was clamped off such that the pressure was maintained inside the tubing section. The mold was then gradually dipped into a deionized hot water bath maintained at 90° C. (±1° C.) to a point just above the proximal waist portion of the mold at a controlled manner. A balloon was formed by radial expansion with internal pressure using a hoop ratio of 5.1. After the balloon formed, the mold was removed from the hot water bath and cooled for approximately 10 sec in a deionized water bath maintained at about 10° C.

Balloons prepared in this manner were subjected to standard burst tests by measuring the double wall thickness of the deflated balloon, inflating the balloon at incrementally increasing pressures and measuring the outside diameter at each increment until the balloon burst. Burst strength, distension and balloon wall strength were calculated from the data obtained. Average results are given in Table 1.

Example 2

The product of this example is a 3.00 mm balloon made from Pebax® 7033. The tubing sections had an OD of 0.0290 inch and an ID of 0.0179 inch. A 3.00 mm size mold was used to produce the balloons. These 3.00 mm balloons were made by the same procedure used in example 1, except for the water bath temperature and internal blowing pressure. The water bath temperature and the pressure were maintained at 95° C. and 300 psi, respectively. The hoop ratio of the balloon was 6.2. The results of testing for burst, distension and wall strength are also listed in Table 1.

Example 3

The product of this example is a 3.00 mm balloon made from Pebax® 7033. The tubing sections had an OD of 0.0316 inch and an ID of 0.0179 inch. A corresponding size mold was used to mold balloons. In this example, 90° C. water bath and 400 psi internal blowing pressure were used. The test results provided in Table 1 show that these balloons gave a higher burst pressure than the previous examples.

Example 4

The product of this example is a 3.00 mm balloon made from Pebax® 7033. The tubing sections had an OD of 0.0320 inch and an ID of 0.0215 inch. A 3.00 mm size mold was used to produce the balloons. The same molding conditions described in example 2 were used except that the tubing was prestretched at room temperature before molding balloons. The prestretch stretching ratio λ was 1.5 in this example. The test results of this example are listed in Table 1.

Example 5

Balloons having 2.0–3.0 mm diameters were prepared from Pebax® 7033 using hoop ratios of 4.6, 5.1 and 6.7. The balloons were expanded incrementally at 37° C. until they burst. The results, plotted in FIG. 1, show semi-compliant curves with very high burst strengths ranging from 15–18 atm and maximum distensions at burst of 24%–45%.

Example 6

In this example, balloons were made from Pebax® 6333. This polymer has a Shore D hardness of 63, a flexural modulus of 49,000, an ultimate tensile strength of 8,100 psi and an ultimate elongation of 300%. The same balloon forming procedure as in example 1 was used, except as noted below. The product of this example is a 2.5 mm balloon. The tubing sections had an OD of 0.0316 inch and an ID of 0.0179 inch. A 2.5 mm size mold was used to produce the balloons. In this example, a 95° C. water bath and a 300 psi internal blowing pressure were used. The hoop ratio for blowing the balloon was 5.5. The results of burst, distension and wall strength are shown in Table 2.

Example 7

Pebax® 6333 tubing with an OD of 0.0310 inch and an ID of 0.0170 inch was used to produce 3.0 mm balloon. The water bath temperature was 90° C. and the internal blow pressure was 300 psi. The hoop ratio for blowing the balloon was 6.9. Test results are shown in Table 2.

TABLE 1

Burst and Distension Test Results of Pebax ® 7033 Material (averages of at least 5 balloons).

| Example | Balloon Size (mm) | Single Wall Thickness (inch) | Burst Pressure (psi) | Distension 88 psi-Burst (%) | Distension 88 psi–132 psi (%) | Distension 88 psi–176 (psi) | Wall Strength |
|---|---|---|---|---|---|---|---|
| 1 | 2.25 | 0.00042 | 230 | 21.3 | 4.2 | 10.9 | 25400 |
| 2 | 3.00 | 0.00047 | 230 | 12.7 | 3.2 | 7.1 | 29200 |
| 3 | 3.00 | 0.00060 | 260 | 12.8 | 3.6 | 6.9 | 25900 |
| 4 | 3.00 | 0.00049 | 220 | 23.5 | 4.4 | 9.0 | 26300 |

TABLE 2

Burst and Distension Test Results of Pebax ® 6333 Material (averages of at least 5 balloons).

| Example | Balloon Size (mm) | Single Wall Thickness (inch) | Burst Pressure (psi) | Distension 88 psi-Burst (%) | Distension 88 psi–132 psi (%) | Distension 88 psi–176 (psi) | Wall Strength |
|---|---|---|---|---|---|---|---|
| 6 | 2.50 | 0.00058 | 220 | 33.7 | 3.4 | 17.4 | 19900 |
| 7 | 3.00 | 0.00049 | 210 | 17.1 | 4.2 | 9.7 | 26100 |

Example 8

Figure 2:
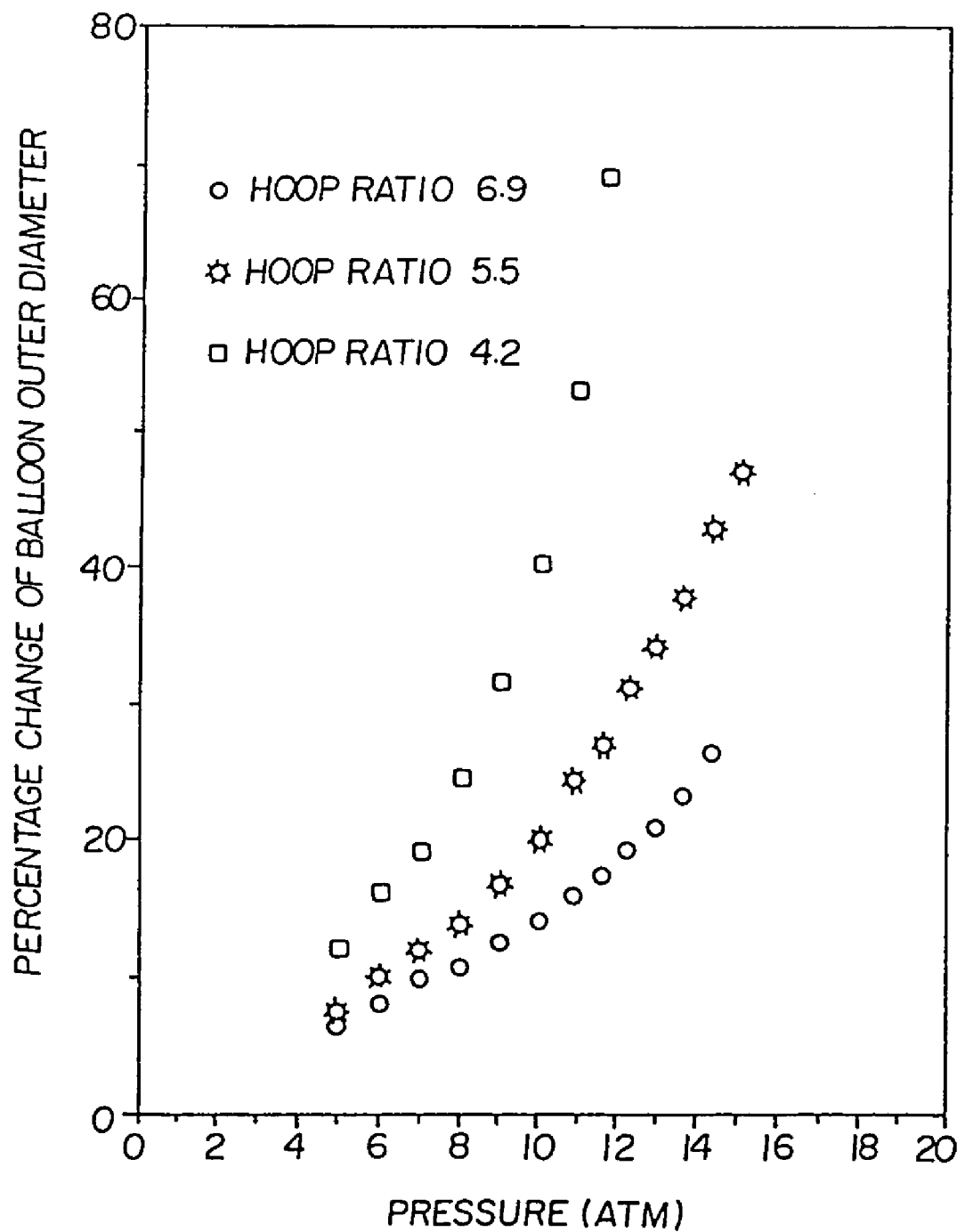
FIG. 2 is a graph as in FIG. 1 using an alternate polyamide/polyether polyester block copolymer to form the balloon of the invention.

Balloons having 2.25–3.0 mm diameters were prepared from Pebax® 6333 using hoop ratios of 4.2, 5.5 and 6.9. The balloons were expanded incrementally at 37° C. until they burst. The results, plotted in FIG. 2, show semi-compliant and compliant curves with burst strengths of 11.5–14 atm and distensions at burst of 23%–69%.

Example 9

The products of this example were 3.00 mm balloons made from Pebax® 6333. The tubing sections had an OD of 0.0350 inch and an ID of 0.0190 inch. A 3.00 mm size mold was used to produce the balloons. Portions of the tubing sections were prestretched at a stretching ratio of 2 ($\lambda=2$) before molding the balloons. The prestretched portions were on either side of a central 8 mm unstretched portion protected during the prestretching operation by a clamp. The unstretched central portion was then formed into a 20 mm long, 3.0 mm diameter balloon body by expansion under pressure in a mold as in the previous examples. The temperature of the water bath was 95° C. and the expansion pressure was 340 psi. The balloons made in this manner had a hoop ratio of 6.2, a single body wall thickness of between 0.0006 and 0.0007 inches, a distal waist wall thickness of between 0.0014 and 0.0021 inches a proximal waist wall thickness of between 0.0014 and 0.0018 inches. The burst pressure of the balloons was about 270 psi. The balloon distension was semi-compliant.

Example 10

The material used in this example was Arnitel EM 740 sold by DSM Engineering Plastics. This polymer had a Shore hardness of 74D, a flexural modulus 120,000 psi, an ultimate tensile strength of 6,400 psi and an ultimate elongation of 340%. 2.25 mm Balloons were prepared from tubing of dimensions OD=0.0270 inches and ID=0.0179 inches. The tubing was necked at two ends and the balloon body portion was unstretched, as described in Example 9. The molding temperature was 80° C. The molding pressure was 290 psi. The molding tension was 50 grams. Balloon properties are given in Table 3.

TABLE 3

Burst and Distension Test Results of Arnitel EM 740 Material

| Example | Balloon Size (mm) | Single Wall Thickness (inch) | Burst Pressure (psi) | Distention 88-Burst % | Distention 88–132 % | Distention 88–176 % | Wall Strength (psi) |
|---|---|---|---|---|---|---|---|
| 10 | 2.25 | 0.00041 | 238 | 34 | 6.2 | 16.7 | 25,700 |

Example 11

The material used in this example was Pebax 7033. The molding temperature was 95° C. The molding pressure was 500 psi. 2.00 mm Balloons were prepared from tubing segments as set forth below. All tubing segments were stretched at room temperature with different stretching ratios and starting tubing dimensions. The unit of ID and OD is inches.

a: the tubing was stretched at $\lambda=2.5$ stretching ratio
        starting ID=0.0130, OD=0.0252
        ending ID=0.0087, OD=0.0177
    b: the tubing was stretched a $\lambda=3.0$ stretching ratio
        starting ID=0.0132, OD=0.0252
        ending ID=0.0081, OD=0.0162
    c: the tubing was stretched at $\lambda=4.5$ stretching ratio
        starting ID=0.0132, OD=0.0262
        ending ID=0.0064, OD=0.0136

The properties of the resulting balloons are set forth in Table 4.

TABLE 4

Burst and Distension Test Results of Pebax 7033 Material

| Example | Balloon Size (mm) | Single Wall Thickness (inch) | Burst Pressure (psi) | Distention 88-Burst % | Distention 88–132 % | Distention 88–176 % | Wall Strength (psi) |
|---|---|---|---|---|---|---|---|
| 11 a | 2.0 | 0.00058 | 279 | 14.6 | 4.0 | 6.5 | 18,900 |
| 11 b | 2.0 | 0.00060 | 279 | 14.6 | 3.5 | 6.6 | 18,300 |
| 11 c | 2.0 | 0.00062 | 353 | 22.2 | 3.0 | 5.4 | 22,600 |

Example 12

The material used in this example was Arnitel EM 740 poly(butylene terephthalate-block-poly(tetramethylene oxide). 2.75 mm Balloons were prepared from tubing of dimensions: OD=0.0390 inches and ID=0.0230 inches. The tubing was stretched at room temperature at $\lambda=4.8$. The dimension of stretched tube was: OD=0.0250 inches and ID=0.0200 inches. The molding temperature was 80° C. The molding pressure was 490 psi. The molding tension was 30 grams. The properties of the resulting balloons are set forth in Table 5.

TABLE 5

Burst and Distension Test Results of Arnitel EM 740 Material

| Example | Balloon Size (mm) | Single Wall Thickness (inch) | Burst Pressure (psi) | Distention 88-Burst % | Distention 88–132 % | Distention 88–176 % | Wall Strength (psi) |
|---|---|---|---|---|---|---|---|
| 12 | 2.75 | 0.00066 | 265 | 43.9 | 8.0 | 18.2 | 21,700 |

Example 13

Pebax 7033 tubes with dimensions 0.0198 inch OD and 0.0339 inch ID is drawn at room temperature with a central region protected by an inserted hypo tube approximately 0.018 inch in diameter and 1.0 inch in length. The tube was drawn until an 8 mm central region remained undrawn. Ten sterilized balloons (3.0 mm in diameter and 20 mm in length) with an average double wall thickness 0.00142 inch are made by radially expanding the 8 mm central tubing portion at 95° C. The resulting burst pressure is 270–280 psi and the distension is 9% over the range 88–176 psi and 16% over the range 88–235 psi.

COMPARATIVE EXAMPLES

Comparative Examples A–C

The material used in this example was Pebax 3533. This polymer has a Shore D hardness of 35 and a flexural modulus of 2,800. Balloons were made by expanding tubes of ID=0.0330 inch and OD=0.0480 inch. The molding temperature was 66° C. The molding pressure was 80 psi. Distension and burst were run at room temperature (22° C.). Balloon properties are set forth in Table 6.

TABLE 6

Burst and Distension Test Results of Pebax 3533 Material

| Comparative Example | Balloon Size (mm) | Single Wall Thickness (inch) | Burst Pressure (psi) | Distention 10-Burst % | Wall Strength (psi) |
|---|---|---|---|---|---|
| A | 1.50 | 0.00495 | 75 | 67 | 450 |
| B | 2.00 | 0.00218 | 50 | 89 | 900 |
| C | 2.50 | 0.00185 | 40 | 73 | 1060 |

Comparative Example D

The material used in this example was Pebax 5533. This polymer has a Shore D hardness of 55 and a flexural modulus of 29,000. 3.00 mm balloons were prepared from tubing sections having an ID of 0.0190 inch and an OD of 0.0360 inch. The molding temperature was 87.5° C. The molding pressure was 300 psi. Portions of the tubing sections were prestretched at a stretching ratio of 2 ($\lambda=2$) before molding the balloons. The prestretched portions were on either side of an 8 mm central unstretched portion protected during the prestretching operation by a hypo tube as in example 13. The unstretched central portion was then formed into a 20 mm long, 3.0 mm diameter balloon body by expansion under pressure in a mold. Balloon properties are set forth in Table 7.

TABLE 7

Burst and Distension Test Results of Pebax 5533 Material

| Comparative Example | Balloon Size (mm) | Single Wall Thickness (inch) | Burst Pressure (psi) | Distention 88-burst % | Distention 88–132 | Distention 29.4-Burst % | Wall Strength (psi) |
|---|---|---|---|---|---|---|---|
| D | 3.00 | 0.00073 | 132 | 17.0 | 17.0 | 44.3 | 10,700 |

Comparative Examples E–G

The material used in this example was Riteflex 640 poly(butylene terephthalate-block-poly)tetramethylene oxide). This polymer has a Shore D hardness of 40 and a flexural modulus of 12,300. Balloons were made by expanding tubes of ID=0.0360 inch and OD=0.0430 inch. The molding temperature was 80° C. The molding pressure was 80 psi. Balloon properties are set forth in Table 8.

TABLE 8

Burst and Distension Test Results of Riteflex 640 Material

| Comparative Example | Balloon Size (mm) | Single Wall Thickness (inch) | Burst Pressure (psi) | Distention 10-Burst % | Wall Strength (psi) |
|---|---|---|---|---|---|
| E | 1.50 | 0.00216 | 80 | 66 | 1100 |
| F | 1.75 | 0.00105 | 65 | 52 | 2100 |
| G | 2.25 | 0.00088 | 60 | 62 | 3020 |

Hybrid Compliance Curve Embodiments

As can be seen from FIGS. 1 and 2, balloons prepared in the manner described above will usually have compliance curves which are generally linear or which provide a slight upwardly increasing slope over their useful range of inflation pressures. In some cases, however, the compliance curve may have a "hybrid" compliance curve, exhibiting a relatively high initial growth rate with pressure up to a transition pressure, after which the slope of the compliance curve drops so that equivalent increases in inflation pressure produce a slower growth rate after the transition. Such a balloon can be characterized by two segments of the curve on either side of the transition region. Suitably the balloon has a compliance curve characterized by a hybrid compliance curve in which a segment of the curve between 6 atm and 10 atm has a slope corresponding to a growth rate of from about 1.5% to about 5% per atm from a reference diameter at 6 atm and a second segment of the curve between 12 and 16 atm has a growth rate of from about 0.3% to about 1.5% per atm from a reference diameter at 12 atm. As illustrated in Example 14, below, balloons made from Pebax® 7233 may be made which have such a property. This property can be advantageous to the user in providing a relatively rapid "compliant" growth profile at low pressures but then slowing to an intermediate or "non-compliant" profile at higher pressures where risk of vessel damage due to oversizing would be greater if the compliant growth rate were maintained. The utility of such a growth profile is discussed in greater detail in U.S. Pat. No. 5,348,538, the entire contents of which are incorporated herein by reference.

Example 14

Figure 3:
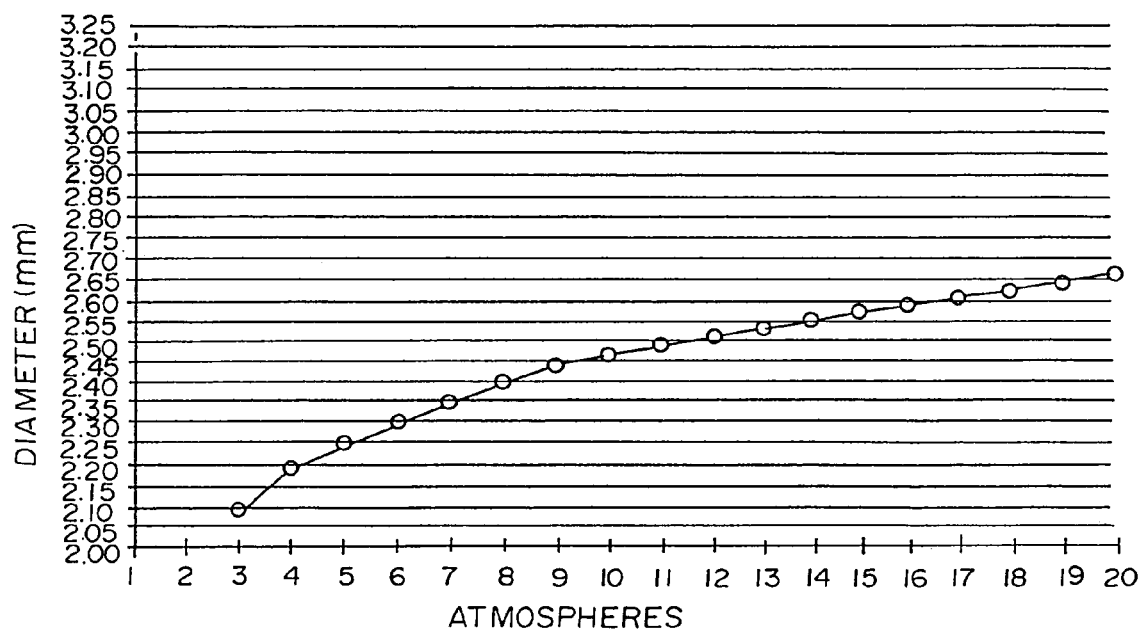
FIG. 3 is a graph as in FIG. 1 using an alternate polyamide/polyether polyester block copolymer which displays a "hybrid" compliance curve.

A 2.5 mm balloon was prepared from Pebax 7233, extruded tube dimensions were ID=0.0156 inch and OD=0.0288 inch. A 15 mm length balloon mold was used. The balloon was formed at 95° C. with a blowing pressure of 450 psi and with 60 grams of tension applied to the tubing during the blowing process. The balloon had a burst pressure of 365 psi, a distension of about 9% over the range of 88–176 psi, and a distension of about 12% over the range 88–235 psi. As illustrated by FIG. 3, the balloon had hybrid compliance curve.

Block Copolymer Blends

Compatible blends of a block copolymer elastomer having a flexural modulus of about 150,000 psi or less, and rigid engineering thermoplastic polymers characterized by a flexural modulus of about 240,000 psi or more can be used to obtain compliance properties which are intermediate between the elastomer and the engineering polymers. For compatibility the block copolymer should have a hard segment of similar chemical structure to the engineering thermoplastic polymer, and preferably the same structure. For instance, thermoplastic melt blend pairs of polyamide elastomers and polyamides; polyurethane elastomers and engineering polyurethanes; aromatic polyester elastomers and aromatic polyesters or copolyesters; and polycarbonate urethane elastomers and polycarbonates may be employed.

Specific examples of polyamide elastomers are the polyamide-polyether-polyester block copolymers described above, in particular Pebax® 6333, Pebax 7033 and Pebax 7233. Specific examples of polyamides characterized by a flexural modulus of about 240,000 psi or more include nylons 11 and 12.

Specific examples of polyurethane elastomers include Tecoflex® aliphatic polyurethane-polyether block copolymers and Tecothane® aromatic polyurethane-polyether polymers, both of which are sold by Thermedics, Inc., and elastomeric polyurethane-polyethers and polyurethane-polyesters sold under the Pellethane® trademark by Dow, for instance Pellethane® 2102, 2103, 2202, 2353–2355 and 2363. Engineering polyurethanes characterized by a flexural modulus of about 240,000 or more include Isoplast® polyurethanes, such as Isoplast® 301, sold by Dow and Tecoplast TP-470 Series resins, which are 82 Shore D, Flex modulus of 300,000 psi aromatic polyurethane-polyethers sold by Thermedics, Inc.

Specific examples of polyester elastomers include polyester urethanes such as Pellethane® 2012, 2202, 2354, and 2355 sold by Dow, and polyester-polyethers such as the Hytrel resins from DuPont, Arnitel EM-740 from DSM and polybutylene naphthanate-polyether block copolymer sold by Teijin. Aromatic polyester polymers include polyethylene terephthalate homopolymers and copolymers such as Traytuf 7357 and Cleartuf 8006, both from Shell, poly-n-propylene terephtalate, polybutylene terephthalate, polyethylene naphthanate, and polybutylene naphthanate. Specific examples of polycarbonate elastomers include Carbothane sold by Thermedics. Polycarbonate engineering thermoplastic resins are available from GE Plastics.

The elastomer/engineering polymer blends may vary in any ratio which will produce a compatible extrudeable mixture. Elastomer/engineering polymer ratios from 99:1 to 1:99 can be employed if compatible.

Examples 15–17 illustrate this aspect of the invention.

Example 15

A PET resin, Shell Traytuf 7357 from Shell was melt blended with a polyester-polyether block copolymer, Arnitel EM 740 from DSM, at a ratio of 75% by weight PET and 25% by weight block copolymer. The blend was extruded into tubing of 0.0146 inch ID and 0.0310 in OD. The tubing was then stretched longitudinally 2.25×. The stretched tubing was then inserted into a 2.50 mm mold and the balloon formed by inflating at 98° C. with pressure. The balloon so formed had a double-wall thickness on cooling of 0.0010 inch. The balloon burst at 21 atm. Its distention from 6 to 12 atm was 8.3% and from 6 atm to burst was 30%.

Example 16

Tubing of the same size as the previous example was prepared from a melt blend of 90% Traytuf 7357 and 10% Arnitel EM 740. The tubing was stretched at a ratio of 3.0×. The stretched tubing was then formed into a balloon as in the previous example. The balloon had a double wall thickness of 0.0008 inch, a burst pressure of 20 atm, a distention from 6 to 12 atm of 6.2% and a distention from 6 atm to burst of 26%.

Example 17

A mixture of Tecothane 1075D (75% by weight) and Tecoplast TP 470 (25% by weight) was extruded at 195° C. into tubing having the dimensions of 0.0195 inch ID and 0.0355 inch (OD). The blended tube was stretched axially at a ratio of 2.25 at 50° C. The stretched tube was then inserted into a 3.00 mm balloon mold and the balloon formed at 85° C. with a blowing pressure of 100 psi and axial tension of 40 grams. The balloon had a double wall thickness of 0.00150 inch; a compliance from 6–12 atm of 16%; and a burst pressure of 235 psi (16 atm).

What is claimed is:

1. A balloon for a medical device formed from a length of tubing of a polymer material by radial expansion of the tubing under pressure, the polymer material comprising a melt blend product of at least two thermoplastic polymers, a first of said polymers being an engineering resin having a flexural modulus of 240,000 psi or greater and a second of said polymers being a block copolymer elastomer having a flexural modulus of about 150,000 psi or less, the block copolymer including at least one block which is structurally similar to the engineering resin, wherein the first and second polymers are a pair selected from the group consisting of engineering polyurethane resins and polyurethane elastomers; aromatic polyesters or copolyesters and aromatic polyester-polyether block copolymers; aromatic polyesters and polyurethane-polyester block copolymers; and polycarbonates and polycarbonate urethane elastomers.

2. A balloon as in claim 1 wherein the first and second polymers are engineering polyurethane resins and polyurethane elastomers, respectively.

3. A balloon as in claim 1 wherein the first and second polymers are aromatic polyesters or copolyesters and aromatic polyester-polyether block copolymers, respectively.

4. A balloon as in claim 1 wherein the first and second polymers are aromatic polyesters and polyurethane-polyester block copolymers, respectively.

5. A balloon as in claim 1 wherein the first and second polymers are polycarbonates and polycarbonate urethane elastomers, respectively.

6. A balloon as in claim 3 wherein the second polymer is characterized as follows:
the block copolymer comprises two or more hard segments of a polyester and two or more soft segments of polyether;
the polyester hard segments are polyesters of an aromatic dicarboxylic acid and a C2–C4 diol, and
the polyether soft segments are polyethers of C2–C10 diols,
the block copolymer has a hardness, Shore D scale, of greater than 60; and
the percentage by weight of the block polymer attributable to the hard segments is between about 50% and about 95%.

7. A balloon as in claim 6 wherein the block copolymer has a Shore D hardness in the range of 65–75 and a flexural modulus in the range of 50,000–120,000 psi.

8. A balloon as in claim 6 wherein said polyether segment, is selected from the group consisting of poly(tetramethylene ether), poly(pentamethylene ether) and poly(hexamethylene ether).

9. A balloon as in claim 6 wherein said polyester segments are polyesters of an acid selected from the group consisting of ortho-, meta- or para- phthalic acid, napthalenedicarboxylic acid and meta-terphenyl-4,4'-dicarboxylic acids and a diol selected from the group consisting of ethylene glycol, 1,3-propane diol and 1,4-butane diol.

10. A balloon as in claim 3 wherein
the first polymer is selected from the group consisting of polyethylene terephthalate, polyethylene naphthanate, polyethylene terephthalate-polyethylene isophthalate copolymer, polybutylene terephthalate and polybutylene naphthanate, and,
the second polymer is poly(butylene terephthalate-block-poly(tetramethylene oxide)).

11. A balloon as in claim 4 wherein the first polymer is selected from the group consisting of polyethylene terephthalate, polyethylene naphthanate, polyethylene terephthalate-polyethylene isophthalate copolymer, polybutylene terephthalate and polybutylene naphthanate, and,
the second polymer is aliphatic polyester polyurethane.

12. A balloon as in claim 1 having a wall strength greater than 20,000 psi.

13. A balloon as in claim 1 having a semi-compliant to non-compliant distension profile whereby as inflation pressure is increased from 6 atm to 12 atm, the balloon expands from a nominal diameter at the 6 atm pressure to an increased diameter at the 12 atm pressure which is from about 5% to about 16% greater than said nominal diameter.

14. A balloon as in claim 1 having a nominal diameter of between 1.5 mm and 4.0 mm, the balloon having a burst pressure of at least 12 atm.

15. A dilation catheter having an elongated tubular body, a balloon mounted on a distal end thereof and means for inflation of the balloon, wherein the balloon is a balloon as in claim 1.

16. A balloon as in claim 2, wherein the first polymer is an aromatic polyurethane-polyether.

17. A balloon as in claim 16, the first polymer having a flexural modulus of about 300,000.

18. A balloon as in claim 2, wherein said second polymer is selected from the group consisting of Aliphatic polyurethane-polyether block copolymers, aromatic polyurethane-polyether polymers, elastomeric polyurethane-polyethers and elastomeric polyurethane-polyesters.

19. A balloon as in claim 16, wherein said second polymer is selected from the group consisting of Aliphatic polyurethane-polyether block copolymers, aromatic polyurethane-polyether polymers, elastomeric polyurethane-polyethers and elastomeric polyurethane-polyesters.

20. A balloon as in claim 2 having a wall strength greater than 20,000 psi.

21. A balloon as in claim 2 having a semi-compliant to non-compliant distension profile whereby as inflation pressure is increased from 6 atm to 12 atm, the balloon expands from a nominal diameter at the 6 atm pressure to an increased diameter at the 12 atm pressure which is from about 5% to about 16% greater than said nominal diameter.

22. A balloon as in claim 2 having a nominal diameter of between 1.5 mm and 4.0 mm, the balloon having a burst pressure of at least 12 atm.

23. A dilation catheter having an elongated tubular body, a balloon mounted on a distal end thereof and means for inflation of the balloon, wherein the balloon is a balloon as in claim 2.

24. A balloon as in claim 2, having a semi-compliant to non-compliant distension profile, whereby, as inflation pressure is increased from 6 atm to 12 atm, the balloon expands from a nominal diameter at the 6 atm pressure to an increased diameter at the 12 atm pressure, which is about 16% greater than said nominal diameter.

25. A balloon as in claim 2, the balloon having a burst pressure of about 16 atm.

26. A balloon as in claim 24, the balloon having a burst pressure of about 16 atm.

27. A balloon as in claim 1, wherein the first and second polymers are a pair selected from the group consisting of aromatic polyesters or copolyesters and aromatic polyester-polyether block copolymers; aromatic polyesters and polyurethane-polyester block copolymers; and polycarbonates and polycarbonate urethane elastomers.

* * * * *